United States Patent
Tang et al.

(10) Patent No.: US 10,858,340 B2
(45) Date of Patent: Dec. 8, 2020

(54) CRYSTAL OF SALT OF QUINAZOLINE DERIVATIVE

(71) Applicants: CHIA TAI TIANQING PHARMACEUTICAL GROUP CO., LTD., Lianyungang (CN); LIANYUNGANG RUNZHONG PHARMACEUTICAL CO., LTD., Lianyungang (CN); CENTAURUS BIOPHARMA CO., LTD., Beijing (CN)

(72) Inventors: Song Tang, Lianyungang (CN); Yizhong Zhu, Lianyungang (CN); Fei Liu, Lianyungang (CN); Jie Zhou, Lianyungang (CN); Zhilin Chen, Lianyungang (CN); Hongjiang Xu, Lianyungang (CN); Xin Tian, Lianyungang (CN)

(73) Assignees: CHIA TAI TIANQING PHARMACEUTICAL GROUP CO. LTD., Lianyungang (CN); LIANYUNGANG RUNZHONG PHARMACEUTICAL CO., LTD., Lianyungang (CN); CENTAURUS BIOPHARMA CO., LTD., Beijing (CN)

(*) Notice: Subject to any disclaimer, the term of this patent is extended or adjusted under 35 U.S.C. 154(b) by 0 days.

(21) Appl. No.: 16/327,640

(22) PCT Filed: Aug. 24, 2017

(86) PCT No.: PCT/CN2017/098798
§ 371 (c)(1),
(2) Date: Feb. 22, 2019

(87) PCT Pub. No.: WO2018/036539
PCT Pub. Date: Mar. 1, 2018

(65) Prior Publication Data
US 2019/0185453 A1   Jun. 20, 2019

(30) Foreign Application Priority Data
Aug. 25, 2016   (CN) .......................... 2016 1 0730222

(51) Int. Cl.
*C07D 401/12*   (2006.01)
*C07C 57/145*   (2006.01)
*C07C 51/41*   (2006.01)
*A61K 31/517*   (2006.01)
*A61P 35/00*   (2006.01)

(52) U.S. Cl.
CPC .......... *C07D 401/12* (2013.01); *A61K 31/517* (2013.01); *A61P 35/00* (2018.01); *C07C 51/41* (2013.01); *C07C 57/145* (2013.01); *C07B 2200/13* (2013.01)

(58) Field of Classification Search
CPC ..... C07D 401/12; A61P 35/00; A61K 31/517; C07C 51/41; C07C 57/145
USPC .......................................................... 544/293
See application file for complete search history.

(56) References Cited

U.S. PATENT DOCUMENTS

| | | | |
|---|---|---|---|
| 8,188,102 B2 * | 5/2012 | Lee ...................... | C07D 401/12 514/266.2 |
| 9,725,439 B2 * | 8/2017 | Xiao ..................... | C07D 403/12 |
| 10,231,973 B2 * | 3/2019 | Zhang .................. | C07D 403/12 |
| 2010/0179120 A1 * | 7/2010 | Lee ....................... | C07D 401/12 514/210.18 |
| 2016/0214964 A1 * | 7/2016 | Xiao ..................... | C07D 403/12 |
| 2018/0085369 A1 * | 3/2018 | Zhang .................. | C07D 403/12 |

FOREIGN PATENT DOCUMENTS

| | | | | |
|---|---|---|---|---|
| CN | 104513229 A | 4/2015 | | |
| WO | WO-2015043515 A1 * | 4/2015 | ........... | C07D 403/12 |
| WO | WO-2016150340 A1 * | 9/2016 | ........... | C07D 403/12 |

OTHER PUBLICATIONS

Morissette; Advanced Drug Delivery Reviews 2004, 56, 275-300. (Year: 2004).*
Berge; Journal of Pharmaceutical Sciences 1977, 66, 1-19. (Year: 1977).*
International Search Report in PCT/CN2017/098798, dated Oct. 31, 2017.

* cited by examiner

*Primary Examiner* — Daniel R Carcanague
(74) *Attorney, Agent, or Firm* — Kilpatrick Townsend & Stockton LLP

(57) ABSTRACT

Disclosed are a crystal of a maleate of a compound of formula (I), a preparation method for the crystal, a crystallization composition of same, a pharmaceutical composition of same, and uses thereof in preventing and treating a tumor.

(I)

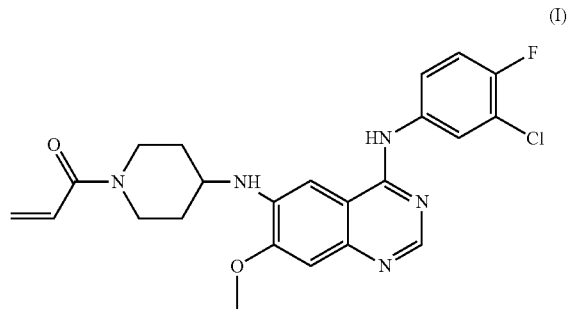

21 Claims, 1 Drawing Sheet

CRYSTAL OF SALT OF QUINAZOLINE DERIVATIVE

CROSS REFERENCE TO RELATED APPLICATION

The present application is a U.S. National Stage Application of PCT/CN2017/098798, International Filing Date Aug. 24, 2017, which claims the priority and benefit of the Chinese invention patent application No. 201610730222.8 filed with the China National Intellectual Property Administration on Aug. 25, 2016, which is incorporated herein by reference in its entirety.

TECHNICAL FIELD

The present application relates to a crystal of a maleate of a quinazoline derivative, a preparation process thereof and a use in the prevention and treatment of a tumor thereof.

BACKGROUND

Lung cancer currently is a malignant tumor with the highest morbidity and mortality worldwide, especially in the developing countries. Lung cancer can be divided into small cell lung cancer and non-small cell lung cancer (NSCLC), where NSCLC accounts for 80% of the total amount of patients with lung cancer. Traditional radiotherapy and chemotherapy lack specificity. These therapies achieve some therapeutic effects and prolong the lifespan of patients, but bring about many side effects, resulting in a significant decrease in the quality of life of patients. In recent years, molecular targeted therapy has made a significant progress in the treatment of lung cancer. The effective drug target for NSCLC is mainly epidermal growth factor receptor (EGFR).

EGFR, a tyrosine kinase receptor, is a member of HER/ErbB family. The HER/ErbB family includes EGFR, HER2, HER3 and HER4, which are consist of three parts: an extracellular ligand-binding domain, a transmembrane domain consisting of single chain, and an intracellular tyrosine kinase domain. EGFR is widely distributed at the surfaces of the mammalian epithelial cells, fibroblasts, glial cells, keratinocytes and so on. EGFR signaling pathway plays an important role in the physiological processes of cells, such as growth, proliferation, differentiation and the like. The functional deficiency of protein tyrosine kinases, such as EGFR, etc., or the abnormality in the activity or cellular localization of key factors in the related signaling pathway, may all cause occurrence of tumors, diabetes, immune deficiencies and cardiovascular diseases.

So far the drugs related to EGFR available in the market includes: Gefitinib (Iressa®), Erlotinib (Tarceva®) and Lapatinib which is an EGFR/HER2 dual inhibitor. The reversible EFGR inhibitors Gefitinib and Erlotinib show favorable therapeutic effects on non-small cell lung cancer patients with EGFR mutation, and they can significantly prolong the progression-free survival (PFS) and overall survival (OS) of the patients. However, recent clinical use indicates that most patients with EGFR mutations have the PFS of no longer than 12 to 14 months, and soon afterwards develop resistance to the EGFR-targeted drugs mentioned above.

Studies have shown that approximately half of the EGFR-targeted drugs develop resistance due to the secondary mutation (T790M) at exon 20 of EGFR. In order to solve the drug resistance problem of the above EGFR-targeted drugs, several irreversible inhibitors, such as Afatinib (BIBW-2992), Canertinib (CI-1033), Neratinib (HKI-272), CO-1686, HM781-36B and the like are developed. CN104513229A discloses a compound of Formula (I), the chemical name of which is $N^6$-(1-acryloyazacyclohexan-4-yl)-$N^4$-(3-chloro-4-fluorophenyl)-7-methoxyquinazoline-4,6-diamine.

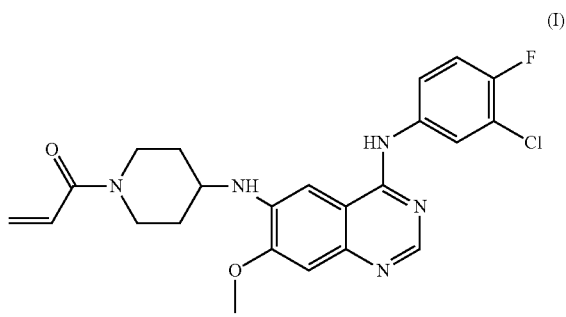 [SMILES: C=CC(=O)N1CCC(Nc2cc3c(Nc4ccc(F)c(Cl)c4)ncnc3cc2OC)CC1]

The compound of Formula I is a selective epidermal growth factor receptor inhibitor. It can competitively bind to the phosphorylation site of tyrosine kinase at an intracellular domain to block an interaction between the phosphorylation site and ATP, and thereby inhibit the tyrosine phosphorylation and a series of downstream signal transduction, and then inhibit the growth of tumor cells. The compound of Formula I therefore can be used to treat various malignant tumors, such as non-small cell lung cancer, breast cancer and the like. See Chinese Patent Application CN104513229A, which is hereby incorporated herein by reference in its entirety.

SUMMARY OF THE INVENTION

The present application provides a crystal of a maleate of the compound of Formula (I), a crystalline composition comprising a crystal of a maleate of the compound of Formula (I), a pharmaceutical composition comprising a crystal of a maleate of the compound of Formula (I) or a crystalline composition thereof, and a pharmaceutical use in the prevention or treatment of a tumor thereof.

DETAILED DESCRIPTION

In the following description, certain specific details are included to provide a thorough understanding of various disclosed embodiments. However, those skilled in the relevant art will recognize that the embodiments may be practiced with other methods, components, materials, and the like, instead of one or more of these specific details.

Unless the context requires otherwise, throughout the specification and claims thereafter, the term "comprise" and English variations thereof, such as "comprises" and "comprising", are to be construed in an open and inclusive sense, i.e., "including, but not limited to".

Reference throughout this specification to "one embodiment", or "an embodiment", or "another embodiment", or "some embodiments" means that a particular referent element, structure, or characteristics described in connection with the embodiment is included in at least one embodiment. Accordingly, the appearances of the phase "in one embodiment", or "in an embodiment", or "in another embodiment", or "in some embodiments" in various places throughout this specification are not necessarily all referring to the same embodiment. In addition, the particular elements, structures, or characteristics may be combined in any suitable manner in one or more embodiments.

It should be noted that, as used in this specification and the appended claims, the singular forms "a". "an" and "the" include plural referents unless the content clearly dictates otherwise. Thus, for example, reference to a reaction in which "a catalyst" is involved includes a single catalyst, or two or more catalysts. Unless otherwise explicitly specified herein, it should also be noted that the term "or" is generally employed in its sense including "and/or".

In an aspect, the present application provides a crystal of a maleate of a compound of Formula (I),

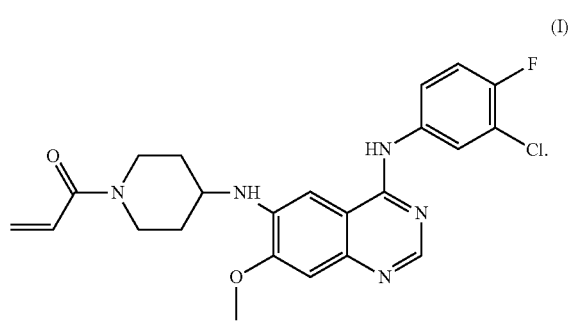 [SMILES: C=CC(=O)N1CCC(Nc2cc3c(Nc4ccc(F)c(Cl)c4)ncnc3cc2OC)CC1]

(I)

In another aspect, the present application provides a crystalline composition comprising a crystal of a maleate of a compound of Formula (I), which accounts for 50 wt % or more, preferably 80 wt % or more, more preferably 90 wt % or more, and most preferably 95 wt % or more by weight of the crystalline composition.

In a further aspect, the present application provides a pharmaceutical composition comprising a therapeutically effective amount of a crystal of a maleate of a compound of Formula (I) or a crystalline composition thereof.

In yet another aspect, the present application provides use of a crystal of a maleate of a compound of Formula (I) or a crystalline composition thereof or a pharmaceutical composition comprising the same in the preparation of a medicament for the prevention or treatment of a tumor.

In still another aspect, the present application provides a method for preventing or treating a tumor, comprising administering to a subject in need thereof a crystal of a maleate of a compound of Formula (I) or a crystalline composition thereof, or a pharmaceutical composition comprising the same.

In another aspect, the present application provides a crystal of a maleate of a compound of Formula (I) or a crystalline composition thereof, or a pharmaceutical composition comprising the same for use in the prevention or treatment of a tumor.

In another aspect, the present application provides use of a crystal of a maleate of a compound of Formula (I) or a crystalline composition thereof, or a pharmaceutical composition comprising the same in the prevention or treatment of a tumor.

In some embodiments of the present application, the crystal of the maleate of the compound of Formula (I) according to the present application is a crystalline Form A of the maleate of the compound of Formula (I) having diffraction peaks at 2θ=6.24°, 7.19°, 14.26°, 18.50°, and 26.80°±0.2° in an X-ray powder diffraction pattern, preferably having diffraction peaks at 2θ=6.24°, 7.190, 14.26°, 18.50°, 22.59°. 26.80°, and 27.64°±0.2°, and more preferably having diffraction peaks at 2θ=6.24°, 7.19°, 14.260, 14.65°, 17.09°, 18.50°, 21.38°, 22.59°, 24.70°, 25.83°, 26.80°, and 27.64°±0.2°.

In some embodiments of the present application, the crystalline Form A of the maleate of the compound of Formula (I) according to the present application has an X-ray powder diffraction pattern as shown in FIG. 1.

In some embodiments of the present application, the crystalline Form A of the maleate of the compound of Formula (I) according to the present application has a melting point of 196° C.-198° C.

In some embodiments of the present application, a molar ratio of the compound of Formula (I) to maleic acid in the crystalline Form A of the maleate of the compound of Formula (I) according to the present application is 1:1.

In another aspect, the present application provides a process for preparing the crystalline Form A of the maleate of the compound of Formula (I):

(1) dissolving the compound of Formula (I) in a mixed solvent of ethyl acetate and an alcohol;

(2) dissolving maleic acid in an alcohol and contacting the acid with the solution of the compound of Formula (I) obtained from step (1); and (3) crystallizing.

In some embodiments of the present application, the present application provides a process for preparing the crystalline Form A of the maleate of the compound of Formula (I):

(1) dissolving the compound of Formula (I) in a mixed solvent of ethyl acetate and an alcohol;

(2) dissolving maleic acid in an alcohol and adding thereto the solution of the compound of Formula (I) obtained from step (1); and (3) crystallizing In some embodiments of the present application, in the processes for preparing the crystalline Form A, the alcohol in step (1) and the alcohol in step (2) are independently selected from one or a mixture of two or more of methanol, ethanol, and isopropanol. In some embodiments of the present application, in the processes for preparing the crystalline Form A, both the alcohol in step (1) and the alcohol in step (2) are ethanol.

In some embodiments of the present application, in the processes for preparing the crystalline Form A, a volume ratio of the alcohol to ethyl acetate in the step (1) is 15~1:1, preferably 8~1:1, and most preferably 2:1.

In some embodiments of the present application, in the processes for preparing the crystalline Form A, a molar ratio of the compound of Formula (I) to maleic acid is 1:1~10, more preferably 1:2~8, and most Preferably 1:5.

In some embodiments of the present application, in the processes for preparing the crystalline Form A, crystallization in the step (3) is performed at 10° C.-40° C., and preferably at 20° C.-30° C.

In some embodiments of the present application, a crystal of the maleate of the compound of Formula (I) according to the present application is a crystalline Form B of the maleate of the compound of Formula (I) having diffraction peaks at 2θ=6.39°, 7.35°, 16.00°, 21.21°, 22.65°, and 27.03°±0.2° in an X-ray powder diffraction pattern, preferably having diffraction peaks at 2θ=6.39, 7.350, 13.37°, 14.97°, 16.00°, 18.58°, 21.21°, 22.65°, 23.98°, 26.12°, 26.50°, 27.03°, and 27.450°±0.2, and more preferably having diffraction peaks at 2θ=6.39°, 7.35°, 13.37°, 14.49°, 14.97°, 16.00°, 17.71°, 18.58°, 19.13°, 21.21°, 22.65°, 23.98°, 24.420, 26.12°, 26.50°, 27.03°, 27.45° and 28.05°±0.2°.

In some embodiments of the present application, the crystalline Form B of the maleate of the compound of Formula (I) according to the present application has an X-ray powder diffraction pattern as shown in FIG. 2.

In some embodiments of the present application, a molar ratio of the compound of Formula (I) to maleic acid in the crystalline Form B of the maleate of the compound of Formula (I) according to the present application is 1:1.

In another aspect, the present application provides a process for preparing the crystalline Form B of the maleate of the compound of Formula (I): dissolving the crystalline Form A of the maleate of the compound of Formula (I) in an organic solvent, and cooling for crystallization.

In some embodiments of the present application, in the process for preparing the crystalline Form B, the organic solvent is selected from the group consisting of dimethyl sulfoxide (DMSO), N,N-dimethylformamide (DMF), and N,N-dimethylacetamide; and preferably, the organic solvent is N,N-dimethylformamide.

EXAMPLES

Figure 1:
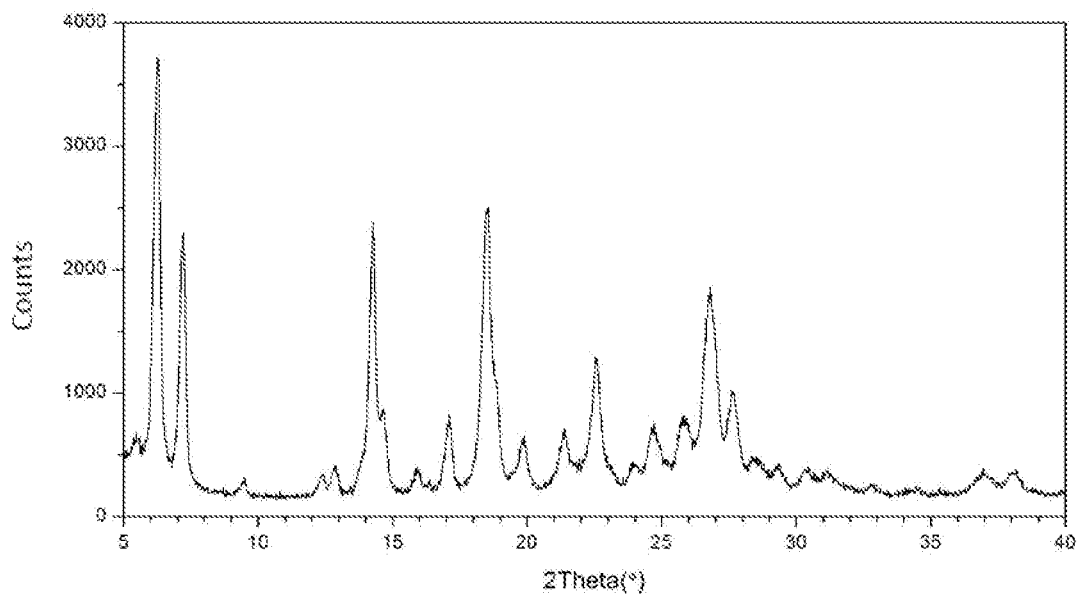
FIG. 1 shows the X-ray powder diffraction pattern (XRPD) of the crystalline Form A of the maleate of the compound of Formula (I).
Figure 2:
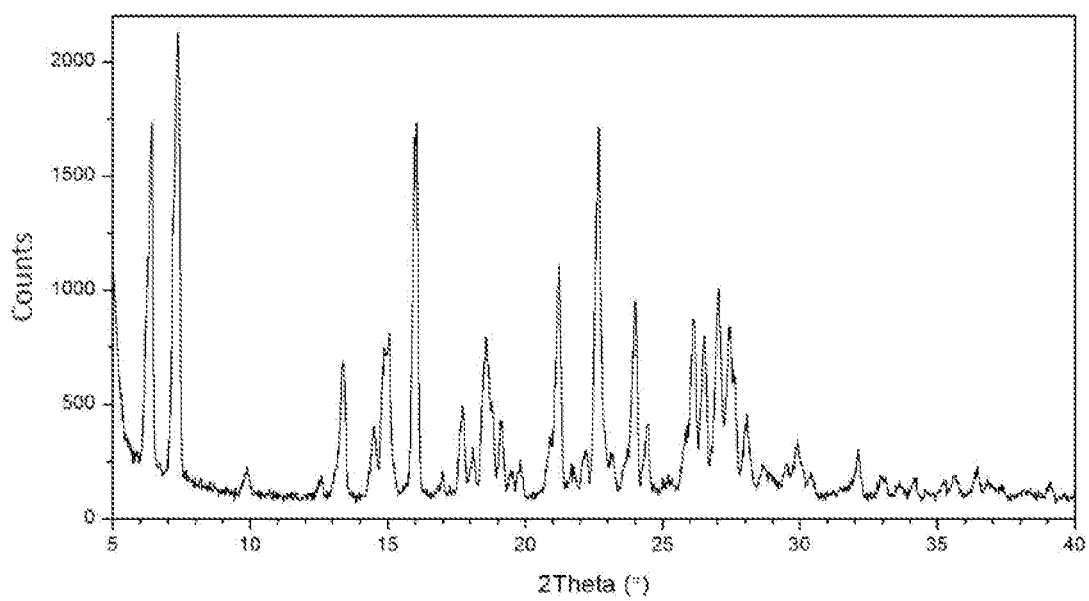
FIG. 2 shows the XRPD of the crystalline Form B of the maleate of the compound of Formula (I).

The present application is described in more detail below through (but not limited to) the following examples and experiments. The compound of Formula (I) used in the examples was prepared according to Example 2 in CN104513229A.

The XRPD was measured using a PHASER BRUKER D2 X-ray powder diffractometer with a wavelength of 1.54060 Å. The melting point was measured using an YRT-3 melting point apparatus (manufactured by Tianjin University). The content was determined by HPLC with reference to Chinese Pharmacopoeia, 2010 edition, Part II, Appendix V D, using octadecylsilane bonded silica gel as a filler, and ammonium formate buffer solution and acetonitrile as a mobile phase; detection wavelength of 260 nm and column temperature of 40° C. The moisture content was determined using a METTLER TOLEDO DL31 Karl Fischer moisture analyzer.

Example 1: Preparation of the Crystalline Form A of the Maleate of the Compound of Formula (I)

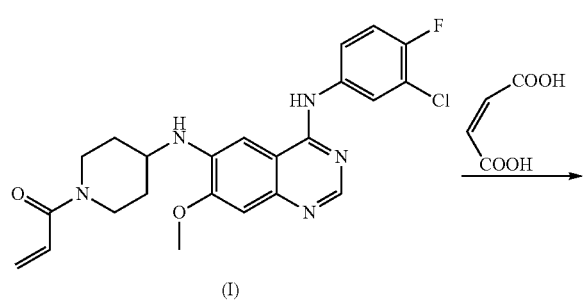

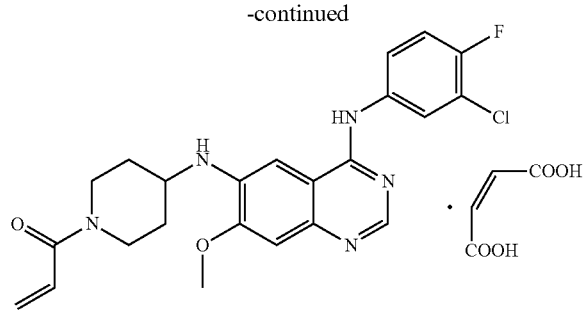

83.1 g of the compound of Formula (I) was dissolved in a mixed solvent of 910 mL of anhydrous ethanol and 455 mL of ethyl acetate at 60° C. 105.8 g of maleic acid and 910 mL of anhydrous ethanol were added to a 3 L reaction flask, and stirred until completely dissolved. To the resulting mixture was added the above solution of the compound of Formula (I) at room temperature, and reacted for 20-24 h at 20-30° C. A large amount of yellow solid was precipitated out, and then filtered. The filter cake was washed with 200 mL of anhydrous ethanol and dried for 24 h in vacuo at 45-55° C. to afford 102.5 g of the crystalline Form A of the maleate of the compound of Formula (I) as a bright yellow solid with a melting point of 196-198° C.

$^1$H-NMR (500 MHz, DMSO-$d_6$): δ15.39 (s, 2H), 10.26 (s, 1H), 8.63 (s, 1H), 8.01 (dd, 1, J=2.4, 6.75 Hz), 7.69-7.72 (m, 1H), 7.52 (t, 1H, J=9 Hz), 7.38 (s, 1H), 7.14 (s, 1H), 6.86 (dd, 1H, J=10.45, 16.65 Hz), 6.15 (s, 2H), 6.12 (d, 1H, J=2.35 Hz), 5.75 (s, 1H), 5.70 (dd, 1H, J=2.15, 10.4 Hz), 4.47 (d, 1H, J=11.2 Hz), 4.14 (d, 1H, J=11.65 Hz), 4.02 (s, 3H), 3.81 (s, 1H), 3.25 (t, 1H, J=11.5 Hz), 2.89 (t, 1H, J=11.2 Hz), 2.06 (s, 2H), 1.50 (s, 2H).

Example 2: Preparation of the Crystalline Form B of the Maleate of the Compound of Formula (I)

10 g of the crystalline Form A prepared in Example 1 was weighed, added to N,N-dimethylformamide, heated to 80° C. and dissolved under stirring, and then hot-filtered. The filtrate was slowly cooled and crystallized for 7 h, and then filtered. The resulting filter cake was washed with 10 ml DMF and dried under for 24 h in vacuo at 55° C. to afford 6.5 g of the crystalline Form B of the maleate of the compound of Formula (I) as a yellow solid.

Example 3: Stability Test of Crystal

The conditions and methods for the stability test of crystal were performed according to the requirements of the Chinese Pharmacopoeia (2010 edition), Part II, Appendix XIX C, Guidelines for Stability Tests of Active Pharmaceutical Ingredients and Pharmaceutical Preparations. The crystalline Form A prepared in Example 1 was used as a test sample. A medicinal low-density polyethylene bag was used as an inner package for a sample, and polyester/aluminum/polyethylene composite bag for pharmaceutical packaging was used as an outer packaging material for a sample. The specific results were shown below.

TABLE 1

| Accelerated test (40° C. ± 2° C., relative humidity of 75% ± 5%) | | | | | |
|---|---|---|---|---|---|
| | Time (Month) | | | | |
| Test items (%) | 0 | 1 | 2 | 3 | 6 |
| Moisture | 0.17 | 0.19 | 0.18 | 0.19 | 0.20 |
| the crystalline Form A of the maleate of the compound of Formula (I) | 99.4 | 99.3 | 99.2 | 99.2 | 99.3 |

TABLE 2

| Long-term test (25° C. ± 2° C., relative humidity of 60% ± 10%) | | | | | | |
|---|---|---|---|---|---|---|
| | Time (Month) | | | | | |
| Test items (%) | 0 | 3 | 6 | 9 | 12 | 18 |
| Moisture | 0.17 | 0.19 | 0.20 | 0.21 | 0.22 | 0.24 |
| the crystalline Form A of the maleate of the compound of Formula (I) | 99.4 | 99.3 | 99.4 | 99.2 | 99.4 | 99.3 |

What is claimed is:

1. A crystal of a maleate of a compound of Formula (I):

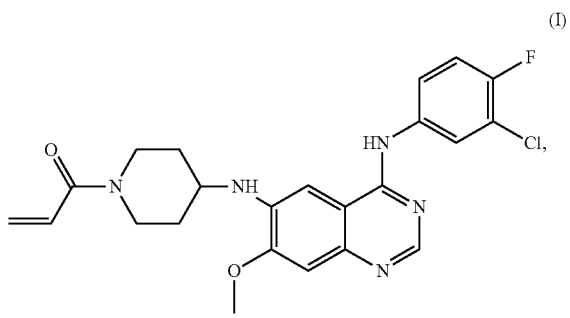 [SMILES: C=CC(=O)N1CCC(Nc2cc3c(Nc4ccc(F)c(Cl)c4)ncnc3cc2OC)CC1]

(I)

wherein the crystal has diffraction peaks at 2θ=6.24°, 7.19°, 14.26°, 18.50°, and 26.80°±0.2° in an X-ray powder diffraction pattern.

2. The crystal of the maleate of the compound of Formula (I) according to claim 1, having a melting point of 196° C.-198° C.

3. A crystal of a maleate of a compound of Formula (I):

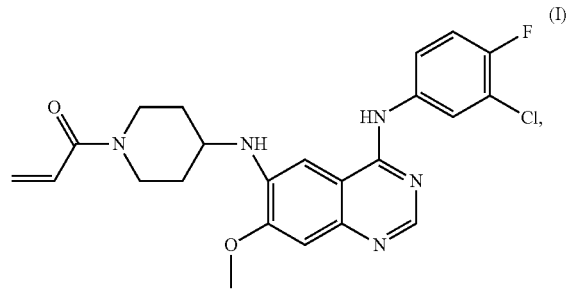 [SMILES: C=CC(=O)N1CCC(Nc2cc3c(Nc4ccc(F)c(Cl)c4)ncnc3cc2OC)CC1]

(I)

wherein the crystal has diffraction peaks at 2θ=6.39°, 7.35°, 16.00°, 21.21°, 22.65°, and 27.03°±0.2° in an X-ray powder diffraction pattern.

4. A process for preparing the crystal of the maleate of the compound of Formula (I) according to claim 1, comprising:

(1) dissolving the compound of Formula (I) in a mixed solvent of ethyl acetate and an alcohol;
(2) dissolving maleic acid in an alcohol and contacting the acid with the solution of the compound of Formula (I) obtained from step (1); and
(3) crystallizing.

5. The process according to claim 4, wherein the alcohol in step (1) and the alcohol in step (2) are independently selected from one or a mixture of two or more of methanol, ethanol, and isopropanol.

6. The process according to claim 4, wherein a molar ratio of the compound of Formula (I) to maleic acid is 1:1~10.

7. The process according to claim 4, wherein a volume ratio of the alcohol to ethyl acetate in step (1) is 15~1:1.

8. A process for preparing the crystal of the maleate of the compound of Formula (I) according to claim 3, comprising: dissolving a crystal of a maleate of the compound of Formula (I), having diffraction peaks at 2θ=6.24°, 7.19°, 14.26°, 18.50°, and 26.80°±0.2° in an X-ray powder diffraction pattern, in an organic solvent, and cooling for crystallization.

9. The process according to claim 8, wherein the organic solvent is selected from the group consisting of dimethyl sulfoxide, N,N-dimethylformamide and N,N-dimethylacetamide.

10. A crystalline composition comprising the crystal of claim 1, which accounts for 50 wt % or more by weight of the crystalline composition.

11. A crystalline composition comprising the crystal of claim 3, which accounts for 50 wt % or more by weight of the crystalline composition.

12. A pharmaceutical composition, comprising a therapeutically effective amount of the crystal of the maleate of the compound of Formula (I) according to claim 1.

13. A pharmaceutical composition, comprising a therapeutically effective amount of the crystal of the maleate of the compound of Formula (I) according to claim 3.

14. A method for the treatment of a tumor in a subject in need thereof, comprising administering to the subject the crystal of the maleate of the compound of Formula (I) according to claim 1.

15. A method for the treatment of a tumor in a subject in need thereof, comprising administering to the subject the crystal of the maleate of the compound of Formula (I) according to claim 3.

16. The crystal of the maleate of the compound of Formula (I) according to claim 1, wherein the crystal has diffraction peaks at 2θ=6.24°, 7.19°, 14.26°, 18.50°, 22.59°, 26.80°, and 27.64°±0.2°.

17. The crystal of the maleate of the compound of Formula (I) according to claim 1, wherein the crystal has diffraction peaks at 2θ=6.24°, 7.19°, 14.26°, 14.65°, 17.09°, 18.50°, 21.38°, 22.59°, 24.70°, 25.83°, 26.80°, and 27.64°±0.2°.

18. The crystal of the maleate of the compound of Formula (I) according to claim 3, wherein the crystal has diffraction peaks at 2θ=6.39°, 7.35°, 13.37°, 14.97°, 16.00°, 18.58°, 21.21°, 22.65°, 23.98°, 26.12°, 26.50°, 27.03°, and 27.45°±0.2°.

19. The crystal of the maleate of the compound of Formula (I) according to claim 3, wherein the crystal has diffraction peaks at 2θ=6.39°, 7.35°, 13.37°, 14.49°, 14.97°, 16.00°, 17.71°, 18.58°, 19.13°, 21.21°, 22.65°, 23.98°, 24.42°, 26.12°, 26.50°, 27.03°, 27.45° and 28.05°±0.2°.

20. The crystal of the maleate of the compound of Formula (I) according to claim 2, wherein a molar ratio of the compound of Formula (I) to maleic acid is 1:1.

21. The crystal of the maleate of the compound of Formula (I) according to claim 4, wherein a molar ratio of the compound of Formula (I) to maleic acid is 1:1.

* * * * *